United States Patent [19]

Shanbrom

[11] 4,305,871

[45] Dec. 15, 1981

[54] METHOD OF SELECTIVELY INCREASING YIELD AND PURITY OF CERTAIN CRYOPRECIPITATE PROTEINS BY HEATING

[76] Inventor: Edward Shanbrom, 2252 Liane La., Santa Ana, Calif. 92705

[21] Appl. No.: 183,364

[22] Filed: Sep. 2, 1980

[51] Int. Cl.$^3$ .............................................. C07G 7/00
[52] U.S. Cl. ............................... 260/112 B; 424/101; 424/177
[58] Field of Search ..................... 260/112 B; 424/101, 424/177

[56] References Cited

U.S. PATENT DOCUMENTS

| | | | |
|---|---|---|---|
| Re. 29,698 | 7/1978 | Fekete et al. | 260/112 B |
| 3,631,018 | 12/1971 | Shanbrom et al. | 260/112 B |
| 3,803,115 | 4/1974 | Fekete et al. | 260/112 B |
| 3,986,506 | 10/1976 | Garber et al. | 128/214 D |
| 4,022,758 | 5/1977 | Andersson et al. | 260/112 B |
| 4,025,618 | 5/1977 | Garber et al. | 424/101 |
| 4,073,886 | 2/1978 | Kehm | 260/112 B |
| 4,086,218 | 4/1978 | Shanbrom et al. | 260/112 B |
| 4,097,473 | 6/1978 | Lewis et al. | 260/112 B X |
| 4,104,266 | 8/1978 | Wickerhauser | 260/112 B |
| 4,105,650 | 8/1978 | Shanbrom et al. | 260/112 B |
| 4,137,223 | 1/1979 | Shanbrom et al. | 260/112 B |
| 4,177,188 | 12/1979 | Hansen | 260/112 |
| 4,189,425 | 2/1980 | Shanbrom et al. | 260/112 B |
| 4,203,891 | 5/1980 | Rock | 260/112 B |
| 4,250,008 | 2/1981 | Mattock | 424/12 X |

OTHER PUBLICATIONS

J. of Biol. Chemistry, vol. 245, No. 21, pp. 5728-5736 (1970), Mosesson et al.,
J. of Biol. Chemistry, vol. 250, No. 16, pp. 6614-6621 (1975), Mosher.
JAMA. vol. 205, 1968, pp. 613-617, Brinkhous et al.
J. of Clinical Investigation, 1957, pp. 605-616, Smith.
Vox Sang 36, 72-76 (1979), Johnson et al.
New Eng. of J. Med., vol. 273, 1965, pp. 1443-1447, Pool et al.
Nature, vol. 203, 1964, p. 312, Pool et al.
Biggs & MacFarlane, "Human Blood Coagulation", F. A. Davis Co. 3d ed., 1962, p. 73.

Primary Examiner—Howard E. Schain

[57] ABSTRACT

AHF and CIg yield and purity in cryoprecipitate concentrate are improved by suspending said cryoprecipitate concentrate in aqueous solution and then subjecting to a heat treatment step at a temperature of from about 45° C. to about 56° C. for a period of from about one minute to about sixty minutes to thereby selectively thermally precipitate the contaminating proteins without substantial loss or AHF of CIg activities and recovering the purified AHF on CIg from the precipitate of contaminating proteins.

9 Claims, No Drawings

4,305,871

METHOD OF SELECTIVELY INCREASING YIELD AND PURITY OF CERTAIN CRYOPRECIPITATE PROTEINS BY HEATING

BACKGROUND OF THE INVENTION

This invention relates to a method for the production of antihemophilic factor (AHF or Factor VIII) and cold-insoluble globulin (CIg or fibronectin).

For a number of years, cryoprecipitation as described by Pool et al. has been a principal method for the isolation and partial purification of AHF. *Nature,* London 203, 312 (1964); *New Eng. J. Med.* 273, 1443–7 (1965). AHF can thus be prepared from single units of plasma in routine blood banking procedures such as in closed bag collection systems as illustrated, e.g., in U.S. Pat. Nos. 3,986,506 and 4,025,618, or concentrates can be prepared commmercially on a large scale as described by Brinkhous et al., *J. Amer. Med. Assn.* 205, 613–617 (1968) and in U.S. Pat. No. 3,631,018.

In order to obtain more highly purified concentrates of AHF, the cryoprecipitation procedures have been combined with fractionation methods that employ various chemical agents such as, e.g., ammonium sulfate, glycine, alcohol, heparin and polycondensed polyglycols such as polyethylene glycol (PEG), polypropylene glycol (PPG) and mixed polyethylene-polypropylene glycols, the latter being block copolymers of ethylene oxide and polyoxypropylene which are available commercially under the trademark Pluronic ® from BASF Wyandotte Chemical Company, Further description of PEG and its use in the production of AHF from cryoprecipitate can be had by reference to U.S. Pat. No. 3,631,018, while similar disclosure of the Pluronic polymers and their use in the production of AHF from cryoprecipitate can be had by reference to U.S. Pat. No. 4,073,886. Disclosures of the use of heparin in the production of AHF from cryoprecipitate can be had by reference to U.S. Pat. Nos. 3,803,115, 4,203,891 and U.S. Pat. No. Re. 29,698.

It is known that during the production of AHF from cryoprecipitate there is an inevitable loss of AHF related to the further purification steps. Although these purification procedures may appear to be simple, they require great care to harvest an optimal amount of AHF. As noted recently by Johnson et al., of the New York University Medical Center, isolation of AHF by large scale techniques results in a maximum yield of about 30% and most large scale producers have obtained a yield of only 20% to 25%. *Vox Sang.* 36, 72–76 (1979). Thus it is desirable to develop some process which would allow removal of unwanted or unnecessary proteins (such as fibrinogen and its denatured and degraded products) from an AHF concentrate without undue loss of the valuable AHF itself. One approach to this goal is to produce a cryoprecipitate which contains increased amounts of AHF as described in recent U.S. Pat. Nos. 4,086,218; 4,105,650; 4,137,223; 4,189,425; and by Johnson et al., *Vox Sang* 36, 72–76 (1979). As disclosed in these patents and publication, small amounts of PEG and/or Pluronic polymers with or without added heparin are employed in the plasma prior to carrying out the freezing process to produce the cryoprecipitate. These procedures thereby result in a higher yield of cryoprecipitate and an associated greater amount of AHF. However, other proteins (e.g., fibrinogen and its derivatives) normally found in the cryoprecipitate are also proportionally increased. Methods normally used to remove the unwanted proteins (such as the precipitation with glycine, PEG and alcohol) unfortunately also remove a proportional amount of AHF by co-precipitation with no real net gain in the final yield of AHF.

Another blood protein which precipitates from plasma in the cold is known as cold-insoluble globulin (CIg or fibronectin). This is an opsonic plasma factor now identified as $\alpha_2$-surface binding globulin. Collection of the starting plasma in the aforesaid polycondensed polyglycols and/or heparin prior to cryoprecipitation also results in precipitation of the CIg with the AHF. Recent comments and reports on the importance of CIg have been published by Rock and Palmer, *Thrombosis Res.* 18, 551–556 (1980) and Anon., *Hospital Pract.* 4(7), 35–36 (1980). See also U.S. Pat. No. 4,210,580.

DESCRIPTION OF THE INVENTION

In accordance with the present invention it has been unexpectedly found that fibrinogen and its denatured and degraded products, which are the primary contaminating proteins of cryoprecipitation, are also uniquely thermoreactive whereby they can be selectively thermally removed from the cryoprecipitate without substantial loss of AHF or CIg activities. According to the method of the invention, the cryoprecipitate is reconstituted in aqueous solution and then subjected to a heat treatment step at a temperature of from about 45° C. to about 56° C., and preferably at about 50° C., for a period of from about one to about sixty minutes, followed by removal of the resulting precipitate of contaminating proteins and recovery of the desired AHF- and CIg-containing supernatant.

The aqueous solution for reconstitution can be, e.g., pyrogen-free water, physiologically normal saline (0.9% NaCl), citrated saline solution (e.g., one part of 0.1 molar sodium citrate in four parts by weight normal saline), tris buffer at pH of about 7, or other physiologically asseptable aqueous solutions which are compatible with AHF and CIg.

As used herein, the cryoprecipitate refers to the precipitate obtained from the freezing and cold thawing of human or animal blood plasma, and separated from the supernatant fraction of the plasma, as well as concentrates of the cryoprecipitate. The cryoprecipitate is preferably obtained by the rapid freezing of fresh plasma although stored plasma can also be used. The freezing is usually carried out at temperatures of from about −20° C. to about −80° C., followed by slow thawing at about 4° C.

During the freezing and cold thawing of plasma to form the cryoprecipitate, the starting plasma preferably is collected and processed with a polycondensed polyglycol such as PEG and/or Pluronic polymer and/or heparin as described in U.S. Pat. Nos. 4,086,218; 4,105,650; 4,137,223; and 4,189,425. In these procedures, preferably from about 0.1 to about 25 grams of said polyol and/or from about 10 to about 2000 units of heparin are used per liter of plasma. PEG 4000 is a preferred polyol but PEG having molecular weights of from about 2000 to about 10,000 also can be used. Pluronic F68 polyol having a polyoxypropylene base molecular weight of about 1750, a polyoxyethylene content of about 80%, and a total molecular weight of about 8750 also is a preferred polyol, but similar such polyols having a polyoxyethylene content as low as about 10% can be used provided that in such case the polyoxypropylene molecular weight is not greater than about 1750. Preferably, the polyoxyethylene content is about 20% or higher and the polyoxypropylene molecular weight is from about 900 to about 4000. The total molecular weight of these block copolymers preferably lies within the range of from about 2000 to about 10,000.

As used herein, one unit of heparin is defined to mean one U.S.P. (United States Pharmacopoeia) unit. The U.S.P. unit of heparin is the quantity that will prevent 1.0 ml of citrated sheep plasma from clotting for one hour after the addition of 0.2 ml of a 1:100 $CaCl_2$ solution. As used herein, the term "heparin" also is meant to include the sodium salt of heparin, the latter substance being preferred due to its water solubility.

Following the heat treatment, the precipitate of contaminating proteins is removed such as by centrifugation, filtration and the like separation procedures, and the clarified supernatant is retained as a purified AHF- and CIg-containing concentrate. This concentrate can then be frozen and stored for later use, or further processed according to conventional procedures known in the art or used directly for administration to a patient.

In those instances where a CIg fraction is desired without AHF, the AHF- and CIg-containing fraction can be heated to about 60° C. for at least about five minutes to inactivate the AHF without substantial loss of the CIg.

The starting material for recovery of a CIg concentrate can also be a cryoprecipitate concentrate from which a substantial portion of the fibrinogen has been precipitated in accordance with the method described in U.S. Pat. No. 4,188,318. According to said method, AHF is separated from from fibrinogen and its denatured and degraded products by collecting the cryoprecipitate in low ionic strength solution. After removal of lipids and prothrombin complex by adsorption, fibrinogen and its denatured and degraded products are then selectively precipitated in the cold while AHF remains in solution. This precipitate also contains CIg. The method of the present invention can then be used on this AHF-poor cryoprecipitate concentrate to inactivate the fibrinogen and its denatured and degraded products without substantial destruction of the CIg.

Although it is not intended to be bound by theory, it is believed that the presence of the polycondensed polyglycol and/or heparin enhances the heat denaturation of fibrinogen while preventing co-precipitation or destruction of AHF and CIg during the heating step.

The following examples will further illustrate the invention although it should be understood that the invention is not limited to these specific examples.

EXAMPLE 1

Fresh human blood is collected in a donor blood bag containing a small amount of anticoagulant solution (ACD or CPD preservative solution). The cells are spun down by centrifugation and the plasma supernatant is expressed into a satellite blood bag. Then 200–250 ml of whole plasma thus collected is admixed with PEG 4000 to a concentration of about 2% by weight of the polyol (Carbowax 4000, Union Carbide). After gentle agitation to ensure complete mixing, the treated plasma is subjected to a temperature between −20° and −50° C. to effect rapid freezing. Once frozen, the plasma is subjected to a temperature between +2° and +4° C. for cold thawing to produce a cryoprecipitate. The supernatant plasma is then removed from the cryoprecipitate by decantation. The retained cryoprecipitate can be frozen and stored for later reconstitution and heat treatment or it can be reconstituted and heat treated immediately as follows:

The cryoprecipitate is first reconstituted with about one to three volumes of pyrogen-free water (or other physiologically acceptable aqueous solution) per gram of cryoprecipitate. Although dissolution can be had at ambient temperature, warming to about 37° C. is used to accelerate dissolution. The reconstituted cryoprecipitate is then subjected to the heat treatment step by heating in a water bath, although other apparatus such as incubating ovens, steam jacketed vessels and the like equipment can be used for larger scale amount of cryoprecipitate. The temperature during this heat treatment step is maintained from about 45° to about 56° C., and preferably at about 50° C. for about one to about sixty minutes. In order to facilitate uniform and optimum heat transfer or distribution, constant mixing of the solution is maintained during the heat treatment step by stirring or other such agitation. The one to sixty minute period of heat treatment can be calculated from the time that opalescence or precipitation is first observer, thus signifying the beginning of fibrinogen denaturation.

Following the aforesaid heat treatment step, the preparation can be centrifuged for clarification, or the supernatant can be directly aspirated into a syringe (which can contain a filter). The final preparation can be administered to the patient directly or refrozen for later use.

When heated as above at about 50° C. for about thirty minutes, about 90% of the fibrinogen is denatured and only about 25% of the AHF activity is lost. When similarly heated for about forty minutes, 100% of the fibrinogen is denatured but still only about 25% of the AHF activity is lost. Thus the method of the invention is able to achieved a desirable selective separation of cryoprecipitate proteins.

EXAMPLE 2

The procedure of Example 1 is repeated except that an equal amount of Pluronic F-68 is substituted for the PEG 4000 in the starting plasma to produce substantially similar results.

EXAMPLE 3

The procedure of Example 1 is repeated except that 125 to 250 units of heparin are added to the 200 to 250 ml of starting plasma with substantially similar results.

EXAMPLE 4

The procedure of Example 2 is repeated except that 125 to 250 units of heparin are added to the 200 to 250 ml of starting plasma with substantially similar results.

EXAMPLE 5

The procedure of Example 1 is repeated except that 125 to 250 units of heparin are added to the 200 to 250 ml of starting plasma without any PEG 4000 or other polycondensed polyglycol added to the plasma with substantially similar results.

Various other examples will be apparent to the person skilled in the art after reading the present disclosure without departing from the spirit and scope of the invention. It is intended that all such further examples be included in the scope of the appended claims.

What is claimed is:

1. The method of improving the yield and purity of a substance selected from the group consisting of AHF and CIg in a cryoprecipitate concentrate of said substance comprising suspending said cryoprecipitate concentrate in aqueous solution and subjecting to heat treatment at a temperature of from about 45° C. to about 56° C. for a period of from about one to about sixty minutes to thereby selectively thermally precipitate contaminating proteins without substantial loss of said AHF or CIg and recovering the purified AHF or CIg by separation from the precipitate of contaminating proteins.

2. The method of claim 1 in which the temperature is maintained at about 50° C.

3. The method of claim 1 in which the starting cryoprecipitate is formed by freezing of plasma which contains from about 0.1 to about 25 grams of a polycondensed polyglycol per liter of said plasma.

4. The method of claim 3 in which the polycondensed polyglycol is PEG having a molecular weight of from about 2000 to about 10,000.

5. The method of claim 4 in which the PEG is PEG 4000.

6. The method of claim 3 in which the polycondensed polyglycol is a mixed polyethylene-polypropylene glycol having a molecular weight of from about 2000 to about 10,000.

7. The method of claim 6 in which the polycondensed polyglycol is a block copolymer containing about 80% of polyoxyethylene units in the molecule and the polyoxypropylene has a base molecular weight of about 1750.

8. The method of claim 1 in which the starting cryoprecipitate is formed by freezing plasma which contains from about 10 to about 2000 units of heparin per liter of plasma.

9. The method of claim 3 in which said plasma contains additionally from about 10 to about 2000 units of heparin per liter of plasma.

* * * * *